(12) United States Patent
Bhide et al.

(10) Patent No.: US 8,148,361 B2
(45) Date of Patent: Apr. 3, 2012

(54) KINASE INHIBITORS

(75) Inventors: Rajeev S. Bhide, Princeton Junction, NJ (US); Anne Marinier, Kirkland (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 407 days.

(21) Appl. No.: 12/513,928

(22) PCT Filed: Nov. 7, 2007

(86) PCT No.: PCT/US2007/083850
§ 371 (c)(1), (2), (4) Date: Oct. 2, 2009

(87) PCT Pub. No.: WO2008/060907
PCT Pub. Date: May 22, 2008

(65) Prior Publication Data
US 2010/0041636 A1 Feb. 18, 2010

Related U.S. Application Data

(60) Provisional application No. 60/865,181, filed on Nov. 10, 2006.

(51) Int. Cl.
*A61K 31/437* (2006.01)
*A61K 31/397* (2006.01)
*C07D 471/04* (2006.01)
*A61P 35/00* (2006.01)
*A61P 7/00* (2006.01)

(52) U.S. Cl. .............. 514/210.21; 514/300; 546/113
(58) Field of Classification Search ............. 514/210.21, 514/300; 546/113
See application file for complete search history.

(56) References Cited

FOREIGN PATENT DOCUMENTS
WO WO 03/099820 12/2003
WO WO 2004/001059 12/2003
WO WO 2006/015123 2/2006

*Primary Examiner* — Janet Andres
*Assistant Examiner* — Niloofar Rahmani
(74) *Attorney, Agent, or Firm* — Elliot Korsen

(57) ABSTRACT

The present invention provides compounds of Formula (I), and pharmaceutically acceptable salts thereof. The Formula (I) compounds inhibit the tyrosine kinase activity of growth factor receptors such as VEGFR-2, FGFR-1 and IGFR-1, thereby making them useful as anti-cancer agents. The formula (I) compounds are also useful for the treatment of other diseases associated with signal transduction pathways operating through growth factor receptors.

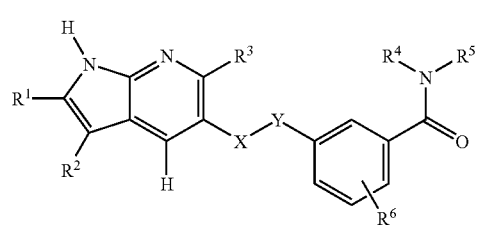

5 Claims, No Drawings

KINASE INHIBITORS

FIELD OF THE INVENTION

This invention relates to compounds that inhibit the protein tyrosine kinase activity of growth factor receptors such as c-Met, VEGFR-2, FGFR-1, IGFR-1 and non-receptor kinases such as SRC kinases thereby making them useful as anti-cancer agents. The pharmaceutical compositions that comprise these compounds are also useful in the treatment of diseases, other than cancer, which are associated with signal transduction pathways operating through growth factor and anti-angiogenesis receptors such as c-Met and VEGFR-2.

BACKGROUND OF THE INVENTION

Normal angiogenesis plays an important role in a variety of processes including embryonic development, wound healing, obesity and several components of female reproductive function. Undesirable or pathological angiogenesis had been associated with disease states including diabetic retinopathy, psoriasis, rheumatoid arthritis, atheroma, Kaposi's sarcoma and haemangioma, asthma, cancer and metastatic disease. Alteration of vascular permeability is thought to play a role in both normal and pathophysiological processes.

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified. One of these subfamilies is presently comprised of the fms-like tyrosine kinase receptor, Flt or Flt1 (VEGFR-1), the kinase insert domain-containing receptor, KDR (also referred to as Flk-1 or VEGFR-2), and another fms-like tyrosine kinase receptor, Flt4 (VEGFR-3). Two of these related RTKs, Flt and KDR, have been shown to bind vascular endothelial growth factor (VEGF) with high affinity. Binding of VEGF to these receptors expressed in heterologous cells had been associated with changes in the tyrosine phosphorylation status of cellular proteins and calcium fluxes. VEGF, along with acidic and basic fibroblast growth factor (aFGF & bFGF) have been identified as having in vitro endothelial cell growth promoting activity. It is noted that aFGF and bFGF bind to and activate the receptor tyrosine kinase termed FGFR-1. By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis and vascular permeability.

In adults, endothelial cells have a low proliferation index except in cases of tissue remodeling, such as wound healing and the female reproductive cycle, and adipogenesis. However in pathological states such as cancer, inherited vascular diseases, endometriosis, psoriasis, arthritis, retinopathies and atherosclerosis, endothelial cells are actively proliferating and organizing into vessels. Upon exposure to angiogenic stimuli with growth factors such as VEGF and bFGF, endothelial cells re-enter the cell cycle, proliferate, migrate and organize into a three-dimensional network. It is now widely accepted that the ability of tumors to expand and metastasize is dependent upon the formation of this vascular network.

The over-expression and activation of VEGFR-2 and FGFR-1 in tumor-associated vasculature has suggested a role for these molecules in tumor angiogenesis. Angiogenesis and subsequent tumor growth is inhibited by antibodies directed against VEGF ligand and VEGF receptors, and by truncated (lacking a transmembrane sequence and cytoplasmic kinase domain) soluble VEGFR-2 receptors. Dominant mutations introduced into either VEGFR-2 or FGFR-1 which result in a loss of enzymatic activity inhibits tumor growth in vivo. Antisense targeting of these receptors or their cognate ligands also inhibits angiogenesis and tumor growth. Recent evidence has elucidated, in part, the temporal requirements of these receptors in tumor growth. It appears that VEGF signaling is critical in early tumor growth and bFGF is more important at a later time associated with tumor expansion.

Hepatocyte growth factor (HGF), also known as scatter factor (SF), because of its ability to disrupt colony formation in vitro, is a mesenchymally derived cytokine known to induce multiple pleiotropic responses in normal and neoplastic cells. These responses are known to include proliferation in both epithelial and endothelial cells, dissociation of epithelial colonies into individual cells, stimulation of motility (motogenesis) of epithelial cells, cell survival, induction of cellular morphogenesis, all critical processes underlying metastasis. HGF has also been reported to promote angiogenesis. In addition, HGF plays a critical role in tissue regeneration, wound healing, and normal embryonic processes, all of which are dependent on both cell motility and proliferation.

Met, also referred to as hepatocyte growth factor receptor (HGFR), is expressed predominantly in epithelial cells but has also been identified in endothelial cells, myoblasts, hematopoietic cells and motor neurons. Over expression of HGF and activation of Met has been associated with the onset and progression in a number of different tumor types as well as in the promotion of metastatic disease. Initial evidence linking Met to cancer has been supported by the identification of kinase domain missense mutations, which predisposes individuals to papillary renal carcinomas (PRC) and hepatocellular carcinomas (HCC). Mutated forms of Met have also been identified in ovarian cancer, childhood HCC, gastric carcinoma, head and neck squamous cell carcinoma, non-small cell lung carcinoma and colorectal metastasis. In addition, further evidence supporting the role of the Met in cancer is based on the overexpression of HGF and Met receptor in various tumors including thyroid, ovarian and pancreatic carcinomas. It has also been demonstrated to be amplified in liver metastases of colorectal carcinomas. TPR-Met (an activated form similar to BCR/Abl in CML) has been described and identified in human gastric carcinoma. In patients with invasive breast carcinoma and in a recent study in non small cell lung cancer patients, expression of either the receptor or ligand is a predictor of decreased survival, further linking Met to tumor progression. In general, most human tumors and tumor cell lines of mesenchymal origin inappropriately express HGFR and/or HGF.

Numerous experimental data support the role of HGF and Met in tumor invasion, growth, survival and progression ultimately leading to metastases. Preclinically, transgenic expression of HGF results in a metastatic phenotype and an amplified/overexpressed Met spontaneously transforms NIH-3T3 cells.

Biological agents, such as ribozymes, antibodies and antisense RNA targeting either HGF or Met have been shown to inhibit tumorogenesis. Thus, selective, small molecule kinase modulators targeting Met are expected to have therapeutic potential for the treatment of cancers in which Met receptor activation plays a critical role in the development and progression of primary tumors and secondary metastases. HGF is also known to regulate angiogenesis, a process critical in tumor growth and dissemination. Therefore, there is a potential for this class of modulators to impact angiogenesis-dependent diseases as well that may include among others, diabetic retinopathy, macular degeneration, obesity and inflammatory disease such as rheumatoid arthritis.

SUMMARY OF THE INVENTION

The invention provides a method for treating a proliferative disease via modulation of protein tyrosine kinase activity of growth factor receptors such as c-Met, VEGFR-2, FGFR-1, IGFR-1 and non-receptor kinases such as SRC kinases by administering to a patient in need of such treatment an effective amount of a compound of Formula I.

DETAILED DESCRIPTION OF THE INVENTION

In accordance with the invention, compounds of Formula I,

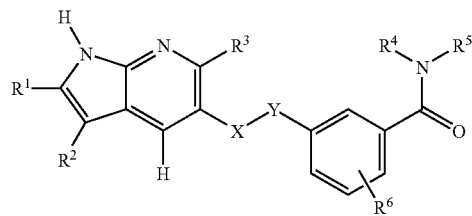

their enantiomers, diastereomers, and pharmaceutically acceptable salts thereof, inhibit the tyrosine kinase activity of growth factor receptors such as VEGFR-2, c-Met, FGFR-1, IGFR-1 and non-receptor kinase such as SRC. In Formula I and throughout the specification, the above symbols are defined as follows:

X and Y are independently —$CH_2$—, —NH—, —S— or —O—, or one of X and Y is absent;

$R^1$, $R^2$ and $R^3$ are independently hydrogen, alkyl, substituted alkyl, cycloalkyl, substituted cycloalkyl, aryl, substituted aryl, heteroaryl, substituted heteroaryl, heterocycloalkyl, substituted heterocycloalkyl, aryloxy or substituted aryloxy;

$R^4$ and $R^5$ are independently hydrogen, alkyl, substituted alkyl, aryl, substituted aryl, cycloalkyl, substituted cycloalkyl, heterocyclyl or substituted heterocyclyl, or $R^4$ and $R^5$ are taken together with the nitrogen atom to which they are attached to form an optionally substituted heterocyclyl ring;

$R^6$ is independently one or more hydrogen, alkyl, substituted alkyl, aryl, substituted aryl, cyano or halogen.

In one embodiment,

X is —$CH_2$—, Y is —NH— or one of X and Y is absent and the other is —O— or —S—;

$R^1$, $R^2$ and $R^3$ are independently hydrogen, aryl, substituted aryl, heteroaryl, substituted heteroaryl, cycloalkyl or substituted cycloalkyl; and $R^4$ and $R^5$ are independently hydrogen, cycloalkyl, substituted cycloalkyl heterocycloalkyl or substituted heterocycloalkyl.

Compounds of the invention include the following:
N-Cyclopropyl-4-fluoro-3-{(2-phenyl-1H-pyrrolo[2,3-b]pyridin-5 yl)methylamino}benzamide,
N-cyclopropyl-2,4-difluoro-5-((2-phenyl-1H-pyrrolo[2,3-b]pyridin-5-yl)methylamino)benzamide,
N-cyclopropyl-4-fluoro-3-((2-phenyl-1H-pyrrolo[2,3-b]pyridin-5-ylamino)methyl)benzamide,
N-cyclopropyl-3-((2-cyclopropyl-1H-pyrrolo[2,3-b]pyridin-5-yl)methylamino)-4-fluorobenzamide,
N-cyclopropyl-4-fluoro-3-((2-(pyridin-3-yl)-1H-pyrrolo[2,3-b]pyridin-5-yl)methylamino)benzamide,
N-cyclopropyl-4-fluoro-3-((2-(pyridin-2-yl)-1H-pyrrolo[2,3-b]pyridin-5-yl)methylamino)benzamide,
N-cyclopropyl-4-fluoro-3-((2-(4-methoxyphenyl)-1H-pyrrolo[2,3-b]pyridin-5-yl)methylamino)benzamide,
N-cyclopropyl-3-((2-(3-(2-(dimethylamino)ethoxy)phenyl)-1H-pyrrolo[2,3-b]pyridin-5-yl)methylamino)-4-fluorobenzamide,
N-(1-(4-fluorophenylsulfonyl)piperidin-4-yl)-3-(2-phenyl-1H-pyrrolo[2,3-b]pyridin-5-yloxy)benzamide,
N-(1-(4-fluorophenylsulfonyl)azetidin-3-yl)-3-(2-phenyl-1H-pyrrolo[2,3-b]pyridin-5-yloxy)benzamide,
N-(1-(4-fluorophenylsulfonyl)azetidin-3-yl)-3-(2-phenyl-1H-pyrrolo[2,3-b]pyridin-5-ylthio)benzamide,
N-(1-(4-fluorophenylsulfonyl)piperidin-4-yl)-3-(2-phenyl-1H-pyrrolo[2,3-b]pyridin-5-ylthio)benzamide,
N-(3-(cyclopropylcarbamoyl)phenyl)-2-phenyl-1H-pyrrolo[2,3-b]pyridine-5-carboxamide,
2-Phenyl-1H-pyrrolo[2,3-b]pyridine-5-carbonitrile,
3-((4-aminopiperidin-1-yl)methyl)-2-phenyl-1H-pyrrolo[2,3-b]pyridine-5-carbonitrile, or a pharmaceutically acceptable salt thereof The invention also provides a method for treating a proliferative disease via modulation of VEGFR-2, c-Met, FGFR-1, IGFR-1 and non-receptor kinases such as SRC activity by administering to a patient in need of such treatment an effective amount of a compound of Formula I, as defined above.

DEFINITIONS

The following are definitions of terms that may be used in the specification. The initial definition provided for a group or term herein applies to that group or term throughout the specification individually or as part of another group, unless otherwise indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or arylalkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively The term "arylsulfonylaminocarbonyl" refers to an arylsulfonyl bonded to an aminocarbonyl.

The terms "aryloxyalkyl", "aryloxycarbonyl" or "aryloxyaryl" refer to an aryloxy bonded to an alkyl or substituted alkyl; a carbonyl; or an aryl or substituted aryl, respectively.

The term "arylalkyl" refers to an alkyl or substituted alkyl in which at least one of the hydrogen atoms bonded to at least one of the carbon atoms is replaced with an aryl or substituted aryl. Typical arylalkyls include, but are not limited to, for example, benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl.

The term "arylalkyloxy" refers to an arylalkyl bonded through an oxygen linkage (—O-arylalkyl).

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocylic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclyl" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, thienothienyl, and the like.

Exemplary substituents include one or more alkyl or arylalkyl groups as described above, $SO_2$aryl or $SO_2$-substituted aryl, or one or more groups described above as alkyl substituents.

Also included are smaller heterocyclyls, such as, epoxides and aziridines.

The term "carbocyclic ring" or "carbocyclyl" refers to stable, saturated, partially saturated or unsaturated, mono or bicyclic hydrocarbon rings that contain 3-12 atoms. Particularly, this includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl and tetrahydronaphthyl. The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The term "alkylsulfone" refers to —$R^kS(=O)_2R^k$, wherein $R^k$ is an alkyl or substituted alkyl.

The term "oxo" refers to the divalent radical =O.
The term "carbamate" refers to the group —$OC(=O)NH_2$.
The term "amide" refers to the group —$C(=O)NH_2$.
The term "sulfonamide" refers to the group —$SO_2NH_2$.

The terms "substituted amide", "substituted sulfonamide", or "substituted carbamate" refer to an amide, sulfonamide, or carbamate, respectively, having at least one hydrogen replaced with a group chosen from alkyl, substituted alkyl, alkenyl, substituted alkenyl, cycloalkyl, and substituted cycloalkyl.

A substituted amide, for example, refers to the group —$C(=O)NR^mR^n$ wherein $R^m$ and $R^n$ are independently selected from H, alkyl, substituted alkyl, alkenyl, substituted alkenyl, cycloalkyl, and substituted cycloalkyl, provided at least one of $R^m$ or $R^n$ is a substituted moiety.

A substituted sulfonamide, for example, refers to the group —$SO_2NR^oR^p$ wherein $R^o$ and $R^p$ are independently selected from alkyl, substituted alkyl, alkenyl, substituted alkenyl, cycloalkyl, and substituted cycloalkyl, provided at least one of $R^o$ or $R^p$ is a substituted moiety.

A substituted carbamate, for example, refers to the group —$OC(=O)NR^qR^r$ wherein $R^q$ and $R^r$ are independently selected from alkyl, substituted alkyl, alkenyl, substituted alkenyl, cycloalkyl, and substituted cycloalkyl, provided at least one of $R^q$ or $R^r$ is a substituted moiety.

The term "ureido" refers to the group —$NHC(=O)NH_2$.
The term "cyano" refers to the group —CN.
The terms "cycloalkylalkyl" or "cycloalkylalkoxy" refer to a cycloalkyl or substituted cycloalkyl bonded to an alkyl or substituted alkyl; or an alkoxy, respectivley.

The term "nitro" refers to the group —$N(O)_2$.
The term "thio" refers to the group —SH.
The term "alkylthio" refers to the group —$SR^s$ where $R^s$ is an alkyl, substituted alkyl, cycloalkyl, or substituted cycloalkyl.

The term "thioalkyl" refers to the group —$R^tS$ where $R^t$ is an alkyl, substituted alkyl, cycloalkyl, or substituted cycloalkyl.

The term "alkylsulfonyl" refers to the group —$S(=O)_2R^u$ where $R^u$ is an alkyl, substituted alkyl, cycloalkyl, or substituted cycloalkyl.

The term "alkylsulfinyl" refers to the group —$S(=O)R^v$ where $R^v$ is an alkyl, substituted alkyl, cycloalkyl, or substituted cycloalkyl.

The term "carboxy" refers to the group —$C(=O)OH$.
The terms "carboxyalkoxy" or "alkoxycarbonylalkoxy" refer to a carboxy, or an alkoxycarbonyl, respectively, bonded to an alkoxy.

The term "alkoxycarbonyl" refers to the group —$C(=O)OR^w$ where $R^w$ is an alkyl, substituted alkyl, cycloalkyl, substituted cycloalkyl, aryl, substituted aryl, heteroaryl, or substituted heteroaryl.

The term "arylalkoxycarbonyl" refers to an aryl or substituted aryl bonded to an alkoxycarbonyl.

The terms "alkylcarbonyloxy" or "arylcarbonyloxy" refer to the group —$OC(=O)R^x$, where $R^x$ is an alkyl or substituted alkyl, or an aryl or substituted aryl, respectively.

The term "carbamoyl" refers to the groups —$OC(=O)NH_2$, —$OC(=O)NHR^x$, and/or —$OC(=O)NR^yR^z$, wherein $R^y$ and $R^z$ are independently selected from alkyl and substituted alkyl.

The group —$NR^6(C=O)R^9$ refers to a group where $R^6$ is selected from hydrogen, lower alkyl and substituted lower alkyl, and $R^9$ is selected from hydrogen, alkyl, substituted alkyl, alkoxy, aminoalkyl, substituted aminoalkyl, alkylamino, substituted alkylamino, aryl and substituted aryl.

The term "carbonyl" refers to a $C(=O)$.
The terms "alkylcarbonyl", "aminocarbonyl", "alkylaminocarbonyl" "aminoalkylcarbonyl", or "arylaminocarbonyl" refer to an alkyl or substituted alkyl; an amino; an alkylamino or substituted alkylamino; an aminoalkyl or substituted aminoalkyl; or an arylamino, respectively, bonded to a carbonyl.

The terms "aminocarbonylaryl" or "aminocarbonylalkyl" refer to an aminocarbonyl bonded to an aryl or substituted aryl; or an alkyl or substituted alkyl, respectively.

The term "sulfonyl" refers to the group $S(=O)_2$.

The term "sulfinyl" refers to an $S(=O)$.

The term "carboxyalkyl" refers to an alkyl or substituted alkyl bonded to a carboxy.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Since prodrugs are known to enhance numerous desirable qualities of pharmaceuticals (e.g., solubility, bioavailability, manufacturing, etc.) the compounds of the invention may be delivered in prodrug form. Thus, the invention is intended to cover prodrugs of the claimed compounds, methods of delivering the same and compositions containing the same. "Prodrugs" are intended to include any covalently bonded carriers that release an active parent drug of the invention in vivo when such prodrug is administered to a mammalian subject. Prodrugs of the invention are prepared by modifying functional groups present in the compound in such a way that the modifications are cleaved, either in routine manipulation or in vivo, to the parent compound. Prodrugs include compounds of the invention wherein a hydroxy, amino, or sulfhydryl group is bonded to any group that, when the prodrug of the invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, p. 309-396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113-191 (1991); and c) H. Bundgaard, *Advanced Drug Delivery Reviews*, 8, 1-38 (1992).

It should further be understood that solvates (e.g., hydrates) of the compounds of formula I are also with the scope of the invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that these recited compounds do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the invention that is effective when administered alone or in combination. "Therapeutically effective amount" is also intended to include an amount of the combination of compounds claimed that is effective to inhibit Trk related diseases and/or conditions. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The invention further includes compositions comprising one or more compounds of the invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed., Mack Publishing Company, Easton, Pa., 1985, which is incorporated herein by reference in its entirety.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease In another embodiment, the invention provides a method for treating a proliferative disease via modulation of Met kinase by administering to a patient in need of such treatment an effective amount of a compound of Formula I, as defined above, in combination (simultaneously or sequentially) with at least one other anti-cancer agent. In a preferred embodiment, the proliferative disease is cancer.

Due to the key role protein kinases in the regulation of cellular proliferation in general, inhibitors could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formula I may modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formula I may be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formula I may also be useful in inhibiting tumor angiogenesis and metastasis.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin®) and small molecules such as ZD6474 and SU6668; Vatalanib, BAY-43-9006, SU11248, CP-547632, and CEP-7055; HER 1 and HER 2 inhibitors including anti-HER2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g. Gleevec® and dasatinib (Sprycel®), Casodex® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo [14.1.0]heptadecane-5,9-dione (ixabepilone), [1S-[1R*,3R*(E),7R*,10S*, 11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo [14.1.0]-heptadecane-5,9-dione, and derivatives thereof; CDK inhibitors, antiproliferative cell cycle inhibitors, epidphyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include, cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, exemestane), antihormones, antiprogestogens, antiandrogens (for example, flutamide, nilutamide, bicalutamide, cyproterone acetate), LHRH agonists and antagonists (for example, goserelin acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); Intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine) and taxoids such as Taxol® (paclitaxel), Taxotere® (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the prostate, pancreatic ductal adreno-carcinoma, breast, colon, lung, ovary, pancreas, and thyroid;

tumors of the central and peripheral nervous system, including neuroblastoma, glioblastoma, and medulloblastoma;

hematological malignancies such as acute myelogenous leukemia (AML), and other tumors, including melanoma and multiple myeloma.

The compounds of this invention may also be useful in combination (administered together or sequentially) with known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidylate synthase inhibitors, such as 5-fluorouracil; and antimetabolites, such as methotrexate, other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2).

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of Formula I may also be administered sequentially with known anticancer or cytotoxic agents when a combination formulation is inappropriate. The invention is not limited in the sequence of administration; compounds of Formula I may be administered either prior to or after administration of the known anticancer or cytotoxic agent(s).

Biological Assays

The pharmacological properties of the compounds of this invention may be confirmed by a number of pharmacological assays. The exemplified pharmacological assays which follow have been carried out with the compounds according to the invention and/or their pharmaceutically acceptable salts.
1. VEGFR-2 and FGFR-1 Kinase Assays:

| Reagents | Final Concentration | |
| --- | --- | --- |
| Stock Solution | VEGFR-2 | FGFR-1 |
| Tris pH 7.0 | 20 mM | 20 mM |
| BSA 10 mg/ml | 25 µg/ml | 25 µg/ml |
| MnCl$_2$ (1M) | 1.5 mM | 0.5 mM |
| MgCl$_2$ (1M) | — | 0.5 mM |
| DTT (1M) | 0.5 mM | 0.5 mM |
| Enzyme Stock in 10% glycerol (1 mg/ml) | 7.5 ng/rxn | 30 ng/rxn |
| Poly glu/tyr (10 mg/ml) | 75 µg/ml | 30 µg/ml |
| ATP (1 mM) | 2.5 µM | 1.0 µM |
| γ-ATP (10 µCi/µl) | 0.5 µCi/ml | 0.5 µCi/ml |

Incubation mixtures employed for VEGFR-2 or FGFR-1 assay contain the synthetic substrate poly glu/tyr, (4:1), ATP, ATP-γ-$^{33}$P and buffer containing Mn$^{++}$ and/or Mg$^{++}$, DTT, BSA, and Tris buffer. The reaction is initiated by addition of enzyme and after 60 minutes at room temperature is terminated by the addition of 30% TCA to a final concentration of 15% TCA. Inhibitors are brought to 10 mM in 100% DMSO. Assays are prepared in a 96 well format in quadruplicate. Compounds are diluted 1:500 in 100% DMSO and then 1:10 in water for a final DMSO concentration of 10%. 10 µL are added to rows B-H in a 96 well format of 10% DMSO. 20 µl of compound is added to row A at a concentration 5 fold higher than running conditions. Ten μL are transferred to each row followed by six serial dilutions with mixing, and at row F 10 μL are discarded. Row G is a control with no compound and row H is no compound and no enzyme control. Enzyme and substrate are delivered using a Tomtec Quadra station.

Plates are covered with sticky plate tops, incubated at 27° C. for 60 minutes, and then acid precipitated with TCA for 20 minutes on ice. The precipitate is transferred to UniFilter-96, GF/C microplates using either a Tomtec or Packard Filter-Mate harvester. Activity is determined by quantitating the incorporated radioactivity using a Packard TopCount Microplate Scintillation Counter following the addition of Microscint-20 cocktail into each dried well of the UniFilter microplates.

The instant compounds inhibit VEGFR-2 and FGFR-1 kinases with $IC_{50}$ values between 0.001 to 10 μM. Preferred compounds have $IC_{50}$ values less than 0.3 μM.

2. Met Kinase Assay

| Reagents<br>Stock Solution | Substrate Mix<br>Final Concentration |
|---|---|
| Tris-HCl, (1M, pH 7.4) | 20 mM |
| $MnCl_2$ (1M) | 1 mM |
| DTT(1M) | 1 mM |
| BSA (100 mg/ml) | 0.1 mg/ml |
| polyGlu$_4$/tyr (10 mg/ml) | 0.1 mg/mL |
| ATP (1 mM) | 1 μM |
| γ-ATP (10 μCi/μl) | 0.2 μCi/ml |
| Buffer | Enzyme mix |
| 20 ul 1M DTT | 4 ul GST/Met enzyme(3.2 mg/ml) = 10 ng/rxn |
| 200 ul 1M Tris-HCL, pH 7.4 | qs 12 ml Buffer |
| 20 ul 100 mg/ml BSA | |
| qs 20 ml $H_2O$ | |

Incubation mixtures employed for the Met kinase assay contain the synthetic substrate polyGlu:Tyr, (4:1), ATP, ATP-γ-$^{33}$P and buffer containing $Mn^{++}$ and/or $Mg^{++}$, DTT, BSA, and Tris buffer. Reactions are incubated for 60 minutes at 27° C. and stopped by the addition of cold trichloroacetic acid (TCA) to a final concentration 4%. TCA precipitates are collected onto GF/C unifilter plates (Packard Instrument Co., Meriden, Conn.) using a Filtermate universal harvester (Packard Instrument Co., Meriden, Conn.) and the filters are quantitated using a TopCount 96-well liquid scintillation counter (Packard Instrument Co., Meriden, Conn.). Dose response curves are generated to determine the concentration required to inhibit 50% of kinase activity ($IC_{50}$). Compounds are dissolved at 10 mM in dimethyl sulfoxide (DMSO) and evaluated at six concentrations, each in quadruplicate. The final concentration of DMSO in the assay is 1%. $IC_{50}$ values are derived by non-linear regression analysis and have a coefficient of variance (SD/mean, n=6)=16%.

The compounds of the invention inhibit the Met kinase enzyme with $IC_{50}$ values between 0.01 to 100 μM. Preferred compounds have $IC_{50}$ values less than 1.0 μM, and more preferably, less than about 0.5 μM.

3. IGF-Receptor Tyrosine Kinase Assay

The IGF-1 receptor tyrosine kinase was assayed using the synthetic polymer poly(Glu/Tyr) (Sigma Chemicals) as a phosphoacceptor substrate. Each reaction mixture consisted of a total volume of 50 ul and contained 125 ng of baculovirus expressed enzyme, 2.5 μg of poly(Glu/Tyr), 25 μM of ATP, and 0.1 μCi of [γ-$^{33}$P]ATP. The mixtures also contained 20 mM MOPS, pH 7.0, 5 mM $MnCl_2$, 0.5 mM DDT, and 0.1 mg/ml bovine serum albumin. The reaction mixtures were incubated at 30° C. for 45 minutes and kinase activity was determined by quantitation of the amount of radioactive phosphate transferred to the poly(Glu/Tyr) substrate. Incorporation was measured by the addition of cold trichloroacetic acid (TCA) precipitation of the proteins which were collected onto GF/C unifilter plates (Packard Instrument Co., Meriden, Conn.) using a Filtermate universal harvester and the filters were quantitated using a TopCount 96-well liquid scintillation counter (Packard Instrument Co., Meriden, Conn.). Compounds were dissolved in dimethyl sulfoxide to a concentration of 10 mM and were evaluated at six concentrations, each in triplicate. The final concentration of DMSO added to the kinase assays was 0.5%, which has been shown to have no effect on kinase activity. IC50 values were derived by non-linear regression analysis and have a coefficient of variance (SD/mean, n=6)=16%.

Representative compounds are shown in the following table.

| Example # | VEGFR2<br>IC50 nM | IGF1R<br>IC50 nM |
|---|---|---|
| 1 | 16 | |
| 2 | 64 | |
| 3 | 103 | |
| 4 | 146 | |
| 5 | 17 | |
| 13 | | 199 |

The following examples and preparations describe the manner and process of making and using the invention and are illustrative rather than limiting. It should be understood that there may be other embodiments which fall within the spirit and scope of the invention as defined by the claims appended hereto.

Methods of Preparation

All temperatures are in degrees Celsius (° C.) unless otherwise indicated. All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm).

Analytical Reverse Phase (RP) HPLC was performed using a Phenomenex Luna C18 S5 4.6 mm×50 mm column or a YMC S5 ODS 4.6×50 mm column. In each case a 4 min linear gradient (from 100% A:% 0 B to 0% A:100% B) was used with the following mobile phase system: A=90% $H_2O$/MeOH+0.2% $H_3PO_4$; B=90% MeOH/$H_2O$+0.2% $H_3PO_4$ at flow rate=4 mL/min and detection at 220 nm.

Preparative Reverse Phase (RP) HPLC was performed with a linear gradient elution using $H_2O$/MeOH mixtures buffered with 0.1% trifluoroacetic acid and detection at 220 nm on one of the following columns: Shimadzu S5 ODS-VP 20×100 mm (flow rate=9 mL/min), or YMC S10 ODS 50×500 mm (flow rate=50 mL/min), or YMC S10 ODS 30×500 mm (flow rate=20 mL/min).

All final products were characterized by $^1$H NMR, RP HPLC, electrospray ionization (ESI MS) or atmospheric pressure ionization (API MS) mass spectrometry. $^1$H NMR spectra were obtained on either a 500 MHz JEOL or a 400 MHz Bruker instrument. $^{13}$C NMR spectra were recorded at 100 or 125 MHz. Field strengths are expressed in units of δ (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

During the work up of reactions, the organic extract was dried over magnesium sulfate (MgSO$_4$), unless mentioned otherwise.

The following abbreviations may be used in the following schemes and examples. Et$_2$O; diethyl ether, Na$_2$SO$_4$; sodium sulfate; HCl; hydrochloric acid, NaOH; sodium hydroxide, NaCl; sodium chloride, Pd/C; palladium on carbon, K$_2$HPO$_4$; potassium monohydrogen phosphate, K$_2$CO$_3$; potassium carbonate, NaHCO$_3$; sodium bicarbonate, LiOH; lithium hydroxide, RT; room temperature, TFA; trifluoroacetic acid, NaBH(OAc)$_3$; sodium triacetoxy borohydride, NBS; N-bromosuccinamide, NaOH; sodium hydroxide, BOP; benzotriazol-1-yloxy-tris(dimethylamino)-phosphonium hexafluorophosphate, (dppf)PdCl$_2$; [1,1'-Bis(diphenylphosphino) ferrocene]dichloropalladium(II), complex with dichloromethane.

Certain compounds of Formula I may generally be prepared according to the following Schemes 1-4. The compounds are synthesized readily using synthetic methods known to one skilled in the art. Tautomers and solvates (e.g., hydrates) of the compounds of Formula I are also within the scope of the present invention. Methods of solvation are generally known in the art. Accordingly, the compounds of the instant invention may be in the free or hydrate form, and may be obtained by methods exemplified by the following schemes below.

Step 1: Variously substituted 2-amino-3-halo pyridines (X=halogen) could be coupled with variously substituted acetylenes, e.g. phenylacetylene, in the presence of a catalyst such as (dppf)PdCl$_2$ to give compound 1 of this scheme.

Step 2: Treatment of compound 1 with a base such as potassium-tert-butoxide in a solvent such as N-methylpyrrolidine (NMP) at elevated temperature gives cyclized compound 2.

Step 3: Compound 2 wherein R$_1$=COOH, could be coupled with an amine such as cyclopropylamine in the presence of a coupling reagent such as BOP reagent in a solvent such as dimethyl formamide to give amides of the formula 3.

Step 4: Compound 2 wherein R$_1$=COOH or an ester could be reduced with a reducing agent, such as lithium aluminum hydride (LAH), in an organic solvent, such as tetrahydrofuran, to afford an intermediate alcohol.

Step 5: Oxidation of the alcohol obtained above could be achieved by the treatment of an oxidant, for example manganese dioxide (MnO$_2$), at an elevated temperature in an organic solvent, such as toluene to give aldehyde compound of formula 4.

Step 6: Compound 4 of this scheme could be treated with an amine such as aniline under reductive amination conditions such as sodium triacetoxy borohydride in dichloromethane to give the compound of formula 5.

Scheme 2

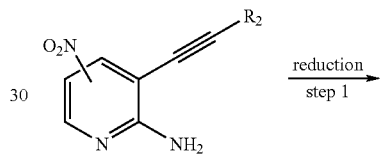

Scheme 1

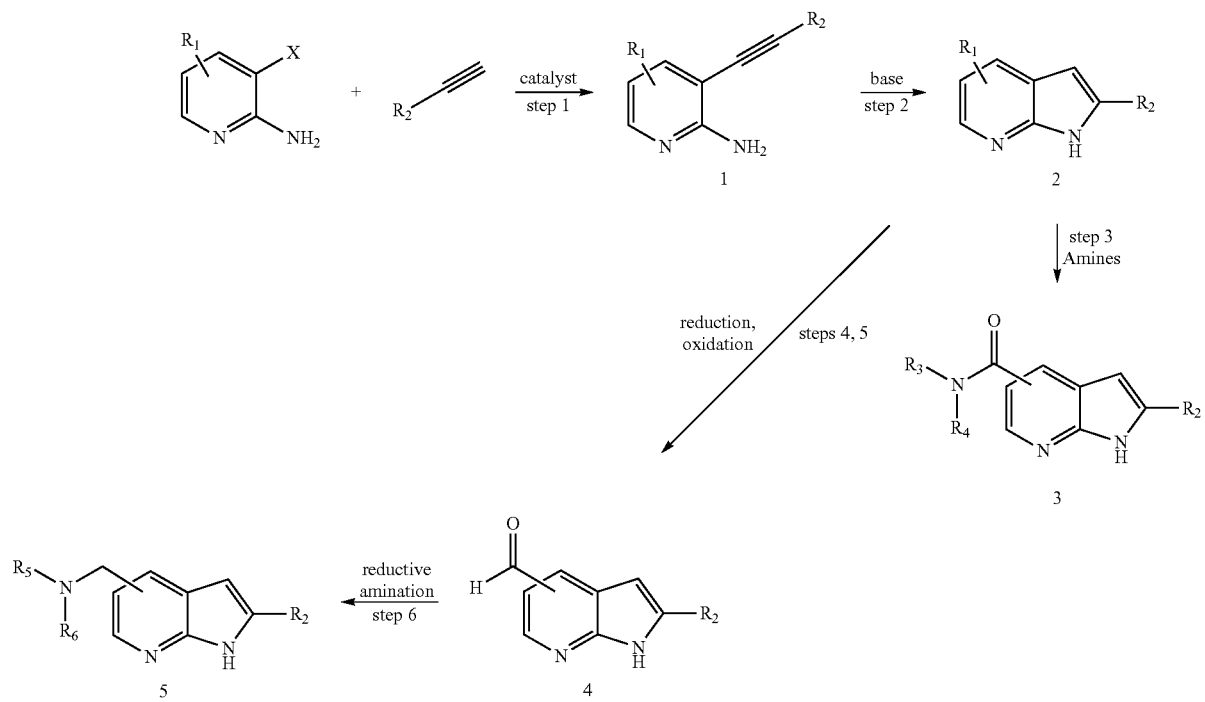

R$_1$ = ester, cyano, nitro etc.;
X = halogen;
R$_2$ = alkyl, aryl, substituted aryl, heteroaryl etc.

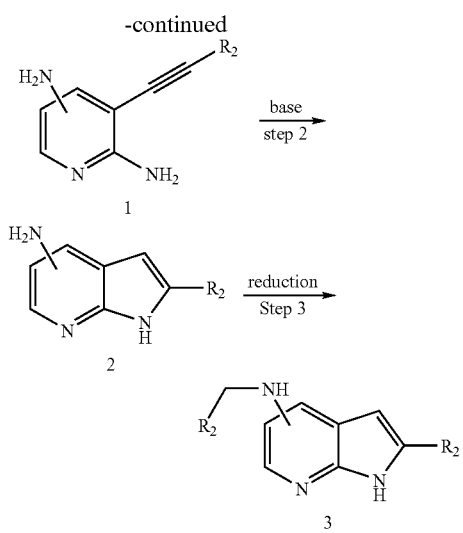

Step 1: Compound 1 of scheme 1 wherein $R_1$ is nitro group, could be reduced with a reducing agent such as iron in an acid such as HCl to afford compound 1 of Scheme 2.

Step 2: Treatment of compound 1 of scheme 2 with a base such as potassium-tert-butoxide in a solvent such as N-methylpyrrolidine (NMP) at elevated temperature gives cyclized compound 2 of scheme 2.

Step 3: Compound 2 of this scheme could be treated with an amine such as aniline under reductive amination conditions such as sodium triacetoxy borohydride in dichloromethane to give the compound of formula 5 of this scheme.

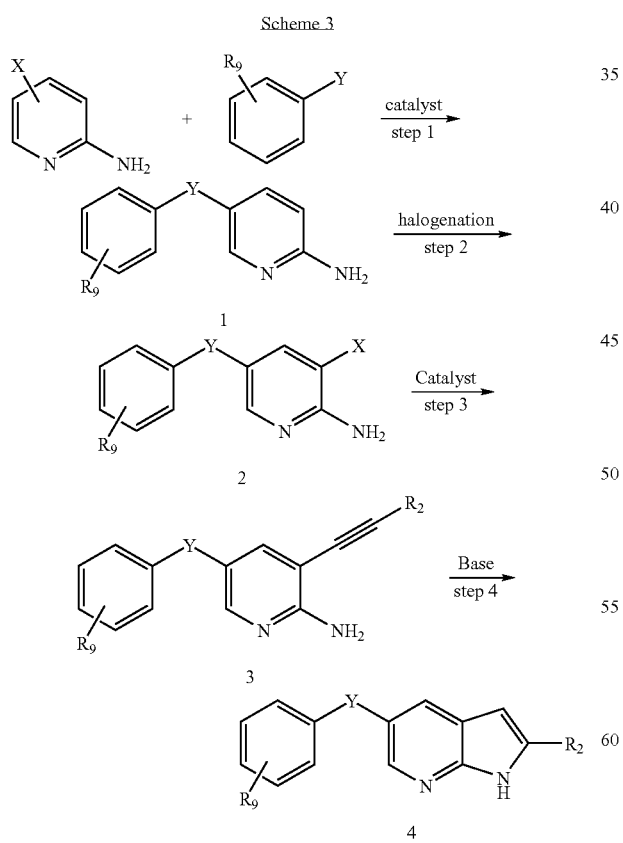

Step 1: 2-Aminopyridine containing a halogen group could be treated with a substituted phenol, substituted thiophenol or substituted aniline such as 3-carbomethoxyphenol in the presence of a catalyst such as CuI (copper iodide) and a base such as cesium carbonate in a solvent such as dioxane at elevated temperature to give compound 1 of scheme 3.

Step 2: Compound 1 of this scheme can then be reacted with a halogenating agent such as NBS in a solvent such as acetonitrile or acetic acid to give compound 2 of scheme 3.

Step 3: Coupling of compound 2 of scheme 3 with substituted acetylenes such as phenylacetylene in the presence of a catalyst such as (dppf)PdCl$_2$ in an inert solvent such as dimethyl formamide at elevated could afford compound of formula 3 of scheme 3.

Step 4: Compound 3 of this scheme then could be cyclized by the treatment of a base such as potassium-tert-butoxide in an inert solvent such as NMP could give the indole derivatives of the formula 4 of scheme 3.

Scheme 4

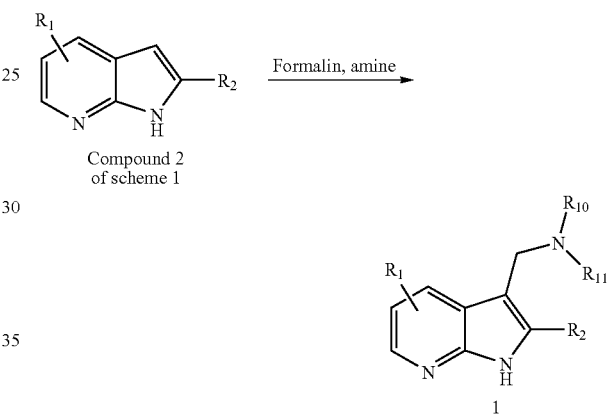

Step 1: Compound 2 of scheme 1 could be treated with an amine such as piperidine in the presence of formalin in a solvent such as acetic acid to obtain compound 1 of scheme 4.

Examples

Example 1

N-Cyclopropyl-4-fluoro-3-{(2-phenyl-1H-pyrrolo[2,3-b]pyridin-5-yl)methylamino}benzamide

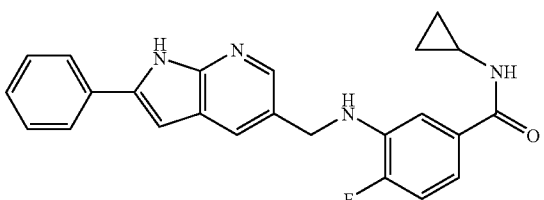

A) A mixture of ethyl 6-amino-5-bromonicotinate (245 mg, 1 mmol), phenylacetylene (220 mg, 2.2 mmol), (dppf)PdCl$_2$ (40 mg), CuI (15 mg), toluene (2 mL), tetrahydrofuran (1 mL) and triethylamine (1 mL) was stirred at 80° C. under argon for 2 h. After cooling to RT, the mixture was washed with water, dried and concentrated in vacuo. The residue was purified by chromatography on silica gel eluting with ethyl acetate in heptanes (1:1) to provide ethyl 6-amino-5-(2-phenylethynyl)nicotinate (205 mg, 77%) as a solid. LC/MS; (M+H)$^+$=267.2

B) To a solution of compound A of this example (266 mg, 1 mmol) in NMP (4 mL) was added potassium tert-butoxide (222 mg, 2 mmol). The reaction was stirred at 80° C. for 1 hr, cooled to RT, and aqueous 1 N HCl (5 mL) was added. The precipitate formed was filtered, washed with water and dried in vacuo to provide 2-phenyl-1H-pyrrolo[2,3-b]pyridine-5-carboxylic acid (215 mg, 81%) as a solid. LC/MS; (M+H)$^+$=239.1.

C) To a mixture of compound B of this example (100 mg, 0.38 mmol) in THF (3 mL) was slowly added lithium aluminum hydride (1M in THF, 1 mL). The mixture was heated to reflux for 2 h, then cooled to 0° C. and water (0.5 mL) was added slowly. The mixture was filtered, the solid was washed with tetrahydrofuran and the filtrate was dried and concentrated to afford a solid which was a 85:15 mixture of the desired product (2-phenyl-1H-pyrrolo[2,3-b]pyridin-5-yl)methanol (100 mg total) and 5-methyl-2-phenyl-1H-pyrrolo[2,3-b]pyridine as a solid. LC/MS; (M+H)$^+$=225 and 209. The crude product was used in the next step without further purification.

D) To a suspension of the crude product C of this example (100 mg) in toluene (10 mL) was added activated MnO$_2$ (150 mg) and the mixture was stirred at 90° C. for 2 h. The mixture was cooled to RT, filtered and the filtrate was concentrated in vacuo. The solid obtained was a 85:15 mixture of the desired product 2-phenyl-1H-pyrrolo[2,3-b]pyridine-5-carbaldehyde (95 mg total) and 5-methyl-2-phenyl-1H-pyrrolo[2,3-b]pyridine as a solid. LC/MS; (M+H)$^+$=223 and 209. The crude product was used in the next step without further purification.

E) To a solution of compound D of this example (95 mg), in a mixture of acetic acid and dichloromethane (1:1, 7 mL) were added 3-amino-N-cyclopropyl-4-fluorobenzamide (50 mg, 0.25 mmol) and NaBH(OAc)$_3$ (70 mg, 0.33 mmol). The mixture was stirred at RT. After 0.5 h, the reaction mixture was concentrated and the residue was purified by preparative RP HPLC. The appropriate fractions were collected and concentrated to remove methanol and saturated solution of NaHCO$_3$ was added to precipitate out the desired product. The solid was filtered and dried in vacuo to give the title compound (18.5 mg) as a solid. LC/MS; (M+H)$^+$=401.2.

Example 2

N-cyclopropyl-2,4-difluoro-5-((2-phenyl-1H-pyrrolo[2,3-b]pyridin-5-yl)methylamino)benzamide

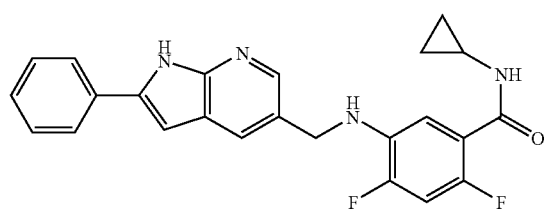

To a solution of compound D of Example 1 (22 mg, 0.1 mmol), in a mixture of acetic acid and dichloromethane (1:1, 1 mL) were added 5-amino-N-cyclopropyl-2,4-difluorobenzamide (30 mg, 0.15 mmol) and NaBH(OAc)$_3$ (30 mg, 0.2 mmol). The mixture was stirred at RT for 1 h. The reaction mixture was concentrated and the residue was purified by preparative RP HPLC. The appropriate fractions were collected and concentrated to remove methanol and saturated solution of NaHCO$_3$ was added to precipitate out the desired product. The solid was filtered and dried in vacuo to give the title compound (6.5 mg) as a solid. LC/MS; (M+H)+=419.2

Example 3

N-cyclopropyl-4-fluoro-3-((2-phenyl-1H-pyrrolo[2,3-b]pyridin-5-ylamino)methyl)benzamide

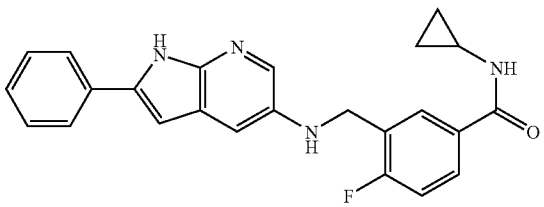

A) The procedure described for the preparation of Example 1A was followed except tetrahydrofuran was not used. Thus, 3-bromo-5-nitropyridin-2-amine (654 mg, 3 mmol) was converted to 5-nitro-3-(2-phenylethynyl)pyridin-2-amine (720 mg). LC/MS; (M+H)$^+$=240

B) To a solution of compound A of Example 3 (180 mg, 0.75 mmol) in ethanol (5 mL) were added iron powder (130 mg, 2.3 mmol) and HCl (3N, 2 mL). The mixture was stirred vigorously at reflux for 1 h. Aqueous NaOH added until alkaline and extracted with ethyl acetate. The organic layer was dried and concentrated in vacuo to afford a solid. This solid was converted to the desired product by the procedure described for Example 1B. The crude solid 2-phenyl-1H-pyrrolo[2,3-b]pyridin-5-amine was dark and contained about 60% of the desired product which was used in the next step without further purification. A small amount of compound was purified by preparative RP HPLC eluting with a mixture of methanol in water containing 0.1% TFA to obtain pure material which was used for recording proton NMR and LC/MS; (M+H)$^-$=210.

C) To a solution of crude compound B of Example 3 (40 mg, 60% purity) in glacial acetic acid (0.5 mL) was added N-cyclopropyl-4-fluoro-3-formylbenzamide (21 mg) and the mixture was stirred at RT. After 30 min, NaBH(OAc)$_3$ (25 mg) was added in three portions and the mixture was vigorously stirred for 1 h at RT. The mixture was concentrated and the residue was purified by preparative RP HPLC eluting with a mixture of methanol in water containing 0.1% TFA. The appropriate fractions were collected and concentrated and neutralized with NaHCO$_3$ solution to obtain the title compound as a solid (6.5 mg). LC/MS; (M+H)$^-$=401.

Example 4

N-cyclopropyl-3-((2-cyclopropyl-1H-pyrrolo[2,3-b]pyridin-5-yl)methylamino)-4-fluorobenzamide

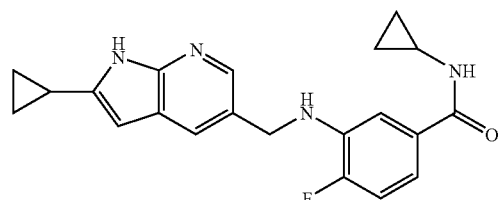

A) Cyclopropyl acetylene (3 mmol) was reacted with ethyl 6-amino-5-bromonicotinate (245 mg, 1 mmol) as described in procedure A of Example 1. Ethyl 6-amino-5-(2-cyclopropylethynyl)nicotinate (180 mg) was obtained as a solid after silica gel column chromatography (EtOAc:hexanes, 1:1). LC/MS; (M+H)$^+$=231.

B) Compound A of Example 4 was converted to 2-Cyclopropyl-1H-pyrrolo[2,3-b]pyridine-5-carboxylic acid (67% yield) as described in procedure B of Example 1. LC/MS; (M+H)$^+$=203.

C) Compound B of Example 4 was converted to (2-cyclopropyl-1H-pyrrolo[2,3-b]pyridin-5-yl)methanol (70% yield) as described in procedure C of Example 1. LC/MS; (M+H)$^+$=189.

D) Compound C of Example 4 was converted to 2-cyclopropyl-1H-pyrrolo[2,3-b]pyridine-5-carbaldehyde (60% yield) as described in procedure D of Example 1. LC/MS; (M+H)$^+$=187.

E) Compound D of Example 4 was converted to the title compound (97% yield) as described in procedure E of Example 1. LC/MS; (M+H)$^+$=365.

Example 5

N-cyclopropyl-4-fluoro-3-((2-(pyridin-3-yl)-1H-pyrrolo[2,3-b]pyridin-5-yl)methylamino)benzamide

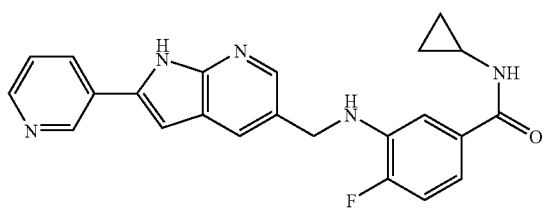

A) To a solution of ethyl 6-amino-5-bromonicotinate (2.31 g, 10 mmol) in tetrahydrofuran (20 mL) at RT was added LAH (10 mL, 1M in tetrahydrofuran) dropwise. After stirring for 1 h, the mixture was quenched with water (0.2 mL) and the resultant precipitate was filtered and washed with ethyl acetate. The filtrate was concentrated in vacuo to afford (6-amino-5-bromopyridin-3-yl)methanol (2.0 g, 99%) as a solid. LC/MS; (M+H)$^+$=203, 205 (1:1 ratio). $^1$H NMR (CD$_3$OD, 300 MHz) δ 7.79 (s, 1H), 7.67 (s, 1H), 4.35 (br S, 2H).

B) To a suspension of compound A of Example 5 (1.9 g, 9.36 mmol) in toluene (20 mL) was added activated MnO$_2$ (2.2 g, 25.6 mmol) and the mixture was heated to 80° C. with vigorous stirring. After 2 h, the mixture was cooled to RT and filtered. The filtrate was concentrated in vacuo to obtain 6-amino-5-bromonicotinaldehyde as a solid (1.8 g, 96%). LC/MS; (M+H)$^+$=203, 201 (1:1 ratio). $^1$H NMR (CD$_3$OD, 300 MHz) δ 9.59 (s, 1H), 8.34 (s, 1H), 8.03 (s, 1H).

C) To a solution of compound B of this example (1.74 g, 8.66 mmol) in a mixture of acetic acid and dichloromethane (1:1, 20 mL) were added 3-amino-N-cyclopropyl-4-fluorobenzamide (1.85 g, 9.5 mmol) and NaBH(OAc)$_3$ (2.42 g, 0.33 mmol) and the mixture was stirred at RT. After 1 h, the reaction mixture was concentrated, the residue was dissolved in EA and washed with saturated K$_2$CO$_3$ solution. The organic layer was dried and concentrated to afford 3-((6-amino-5-bromopyridin-3-yl)methylamino)-N-cyclopropyl-4-fluorobenzamide (2.38 g, 72%) as a solid. LC/MS; (M+H)$^°$=379, 380 (1:1 ratio). $^1$H (CD$_3$OD) δ 7.92 (1H, S), 7.77 (1H, s), 7.20 (1H, M), 7.01 (m, 2H), 4.28 (2H, S), 2.78 (1H, m), 0.76 (2H, m), 0.59 (2H, m).

D) To a suspension of compound C of this example (758 mg, 2 mmol) in toluene (50 mL) were added 3-ethynylpyridine (620 mg, 6 mmol), (dppf)PdCl$_2$ (163 mg complex with dichlromethane), CuI (100 mg), and triethylamine (20 mL) were added. The resulting mixture was stirred at 100° C. under argon for 4 h. After cooling to RT, the mixture was concentrated and the residue obtained washed with ammonia solution, then dissolved in methanol and the mixture was filtered to remove solid impurities. The filtrate was concentrated and the residue was triturated with acetone. The solid was collected and dried in vacuo to afford 3-((6-amino-5-(2-(pyridin-3-yl)ethynyl)pyridin-3-yl)methylamino)-N-cyclopropyl-4-fluorobenzamide (635 mg, 79%) as a solid. LC/MS; (M+H)$^+$=402.

E) The solid obtained above (620 mg, 1.55 mmol) was dissolved in NMP (10 mL) and potassium tert-butoxide (520 mg) was added. The resulting mixture was stirred at 100° C. under argon for 2 h. After cooling to RT, the mixture was acidified with 1 N HCl and diluted with water. The precipitate formed was collected, washed with water and dried. It was then dissolved in methanol (10 mL), 1N HCl (1.5 mL) was added and the solution was concentrated. The residue obtained was refluxed with isopropanol and cooled to afford the title compound (521 mg) as a salt which was a solid. LC/MS; (M+H)$^+$=402.

Example 6

N-cyclopropyl-4-fluoro-3-((2-(pyridin-2-yl)-1H-pyrrolo[2,3-b]pyridin-5-yl)methylamino)benzamide

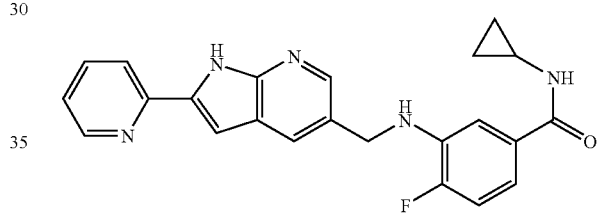

A) 3-((6-amino-5-bromopyridin-3-yl)methylamino)-N-cyclopropyl-4-fluorobenzamide (38 mg, 0.1 mmol) was reacted with 2-ethynylpyridine (0.1 mL) as described in procedure D of Example 5 to afford 3-((6-Amino-5-(2-(pyridin-2-yl)ethynyl)pyridin-3-yl)methylamino)-N-cyclopropyl-4-fluorobenzamide as a solid. It was used without further purification. LC/MS; (M+H)$^+$=402.

B) The crude solid from procedure A of this example was treated with potassium-tert-butoxide (50 mg) in NMP (0.3 mL) as described in procedure E of Example 5. The crude reaction mixture was purified by RP preparative HPLC and the appropriate fractions were collected and concentrated to remove methanol. The remaining solution was treated with saturated NaHCO3 to obtain a precipitate which was filtered, washed with water and dried in vacuo to obtain the title compound (4.7 mg) as a solid. LC/MS; (M+H)$^-$=402.

Example 7

N-cyclopropyl-4-fluoro-3-((2-(4-methoxyphenyl)-1H-pyrrolo[2,3-b]pyridin-5-yl)methylamino)benzamide

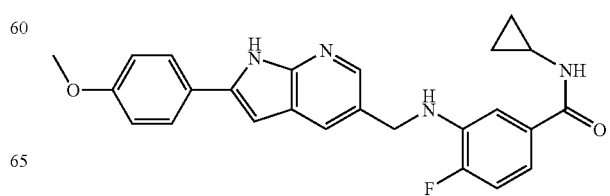

A. The title compound was prepared by using the procedure described for the preparation of Example 6 except 1-ethynyl-4-methoxybenzene was used in place of 2-ethynylpyridine. LC/MS; (M+H)⁻=431.

Example 8

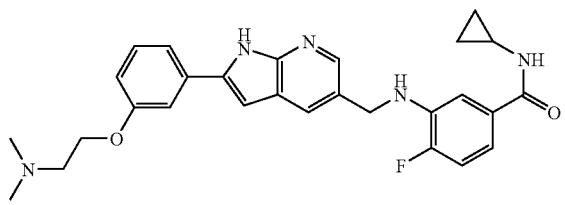

A) The title compound was prepared by using the procedure described for the preparation of Example 6 except 2-(3-ethynylphenoxy)-N,N-dimethylethanamine was used in place of 2-ethynylpyridine. LC/MS; (M+H)⁺=488.

The intermediate 2-(3-ethynylphenoxy)-N,N-dimethylethanamine was prepared as follows.

B) 3-Ethynylphenol (1.18 g, 10 mmol), 2-chloro-N,N-dimethylethanamine (1.44 g, 10 mmol), Cesium carbonate (7.0 g, 21 mmol) was dissolved in dimethyl formamide (20 mL) and the mixture was heated to 65° C. for 1 h. The mixture was cooled to RT and the partitioned between water and dichloromethane. The organic layer was separated, washed with 2N NaOH and then extracted with 1N HCl. The HCl solution was then neutralized with aqueous NaOH and extracted with dichloromethane. The organic layer was dried and concentrated to afford 2-(3-ethynylphenoxy)-N,N-dimethylethanamine (0.6 g) as an oil. LC/MS; (M+H)⁺=190.

Example 9

2-Phenyl-1H-pyrrolo[2,3-b]pyridine-5-carbonitrile

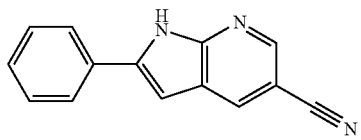

A) To a solution of 6-aminonicotinonitrile (3.6 g, 300 mmol) in glacial acetic acid (50 mL) at RT was added sodium acetate (30 mmol). To the resulting well stirred mixture was added bromine (2.58 mL, 30 mmol) dropwise. After 5 min, a precipitate started to form and the mixture became very thick. Acetic acid (10 mL) was added and the mixture was stirred vigorously for 1 h, poured into cold water (100 mL). The mixture was filtered; the solid was washed with water and dried in vacuo to afford 6-amino-5-bromonicotinonitrile (4.25 g) as a solid. LC/MS; (M+H)⁺=199. Additional solid precipitated from the filtrate after some time which upon filtration and drying gave less pure compound (1.21 g).

B) Compound A (360 mg, 1.82 mmol) of this example was converted to 6-amino-5-ethynylnicotinonitrile (240 mg) in a manner similar to the preparation of compound A of Example 1. LC/MS; (M+H)⁺=220.

C) Compound B of this example (75 mg, 0.34 mmol) was converted to the title compound (65 mg) in a manner similar to the preparation of compound B of Example 1. LC/MS; (M+H)⁺=220.

Example 10

3-((4-aminopiperidin-1-yl)methyl)-2-phenyl-1H-pyrrolo[2,3-b]pyridine-5-carbonitrile

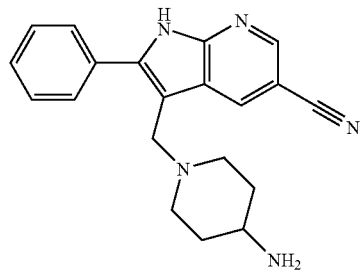

To a solution of the compound prepared in Example 9 (22 mg, 0.1 mmol) in acetic acid (1 mL) were added formalin (0.1 mL) and tert-butyl piperidin-4-ylcarbamate (30 mg, 0.5 mmol). The reaction mixture was stirred at 80° C. for 1 h. The LC/MS showed a peak of m/e=462. Aqueous HCl (3N, 1 mL) was added and the resulting mixture was heated to 100° C. for 4 h. The LC/LC/MS; (M+H)+=analysis indicated the formation of the desired product. The mixture was cooled, concentrated and the residue was purified by preparative RP HPLC eluting with a mixture of methanol in water containing 0.1% TFA. The fractions containing the desired product were collected, concentrated and converted to HCl salt to afford the title compound (40 mg) as a solid. LC/MS; (M+H)⁺=332.

Example 11

N-(1-(4-fluorophenylsulfonyl)piperidin-4-yl)-3-(2-phenyl-1H-pyrrolo[2,3-b]pyridin-5-yloxy)benzamide

A) A procedure described by D. Ma and Q. Cai (Org. Lett. 3799, 2003) was followed. To a solution of 5-bromopyridin-2-amine (346 mg, 2 mmol) in dioxane (10 mL) were added methyl 3-hydroxybenzoate (400 mg, 2.6 mmol), CuI (50 mg), N,N-dimethylglycine (60 mg) and Cs$_2$CO$_3$ (1.0 g). The resulting mixture was heated to 120° C. for 5 h, then cooled and partitioned between water and dichloromethane. The organic layer was separated, dried, and concentrated. The residue was purified by silica gel column eluting with ethyl acetate in dichloromethane (1:1) to obtain methyl 3-(6-aminopyridin-3-yloxy)benzoate (250 mg, 50%) as an oil. LC/MS; (M+H)$^+$=245.

B) To a solution of compound A of this example (122 mg, 0.5 mmol) in acetonitrile (1 mL) was added NBS (100 mg) and the mixture was stirred at RT for 1 h. To the resulting solution was added water (3 mL) and the solution was extracted with ethyl acetate. The organic layer was separated, dried and concentrated. The residue was purified by silica gel column eluting with ethyl acetate in hexanes (1:1) to afford methyl 3-(6-amino-5-bromopyridin-3-yloxy)benzoate (57 mg, 35%) as an oil. LC/MS; (M+H)$^+$=323, 325 (1:1 ratio).

C) Compound B of this example (323 mg, 1 mmol) was converted to methyl 3-(6-amino-5-(2-phenylethynyl)pyridin-3-yloxy)benzoate (320 mg, 93%) in manner similar to the procedure described for the preparation of compound A of Example 1 except tetrahydrofuran was not used. LC/MS; (M+H)$^+$=345.

D) The above compound C of this example (320 mg, 0.93 mmol) was converted to 3-(2-phenyl-1H-pyrrolo[2,3-b]pyridin-5-yloxy)benzoic acid (265 mg, 92%) in manner similar to the procedure described for the preparation of compound B of Example 1. LC/MS; (M+H)+=331.

E) To a solution of tert-butyl piperidin-4-ylcarbamate (200 mg, 1 mmol) in tetrahydrofuran (5 mL) were added 4-fluorobenzenesulfonyl chloride (195 mg, 1 mmol), triethylamine (0.2 mL) and the mixture was stirred at RT. After 2 h, the volatiles were removed in vacuo and the water was added to the residue. The solid formed was filtered, washed successively with water, 1N HCl, and water to afford tert-butyl 1-(4-fluorophenylsulfonyl)piperidin-4-ylcarbamate (350 mg, 98%) as a solid. LC/MS; (M+H)$^+$=359.

F) To a solution of compound E of this example (250 mg) in dichloromethane (0.5 mL) was added TFA (0.5 mL) and stirred at RT. After 1 h, the volatiles were removed in vacuo and the residue was treated with aqueous 2N NaOH and extracted with dichloromethane. The organic layer was separated, dried and concentrated to afford 1-(4-fluorophenylsulfonyl)piperidin-4-amine as a solid. LC/MS; (M+H)$^+$=259 which was used without further purification.

G) To a solution of compound F of this example (52 mg, 0.2 mmol) in dimethyl formamide (1 mL) were added acid compound D of this example (66 mg, 0.2 mmol), BOP (100 mg), and triethylamine (0.1 mL). The resulting mixture was stirred at RT for 1 h, diluted with water and the precipitate was filtered. The solid was washed successively with water, methanol, dichloromethane, dried in vacuo, and purified by RP HPLC eluting with a mixture of methanol in water containing 0.1% TFA to obtain the title compound (25 mg) as a solid. LC/MS; (M+H)$^+$=571.

Example 12

N-(1-(4-fluorophenylsulfonyl)azetidin-3-yl)-3-(2-phenyl-1H-pyrrolo[2,3-b]pyridin-5-yloxy)benzamide

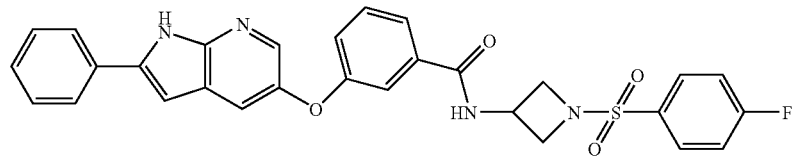

A) tert-Butyl azetidin-3-ylcarbamate (344 mg, 2 mmol, 30% purity) was converted to 1-(4-fluorophenylsulfonyl)azetidin-3-amine (45 mg) by a procedure similar to the preparation of compound F of Example 11 from tert-butyl piperidin-4-ylcarbamate.

B) Compound A of this example was treated with compound D of Example 11 by a procedure similar to the preparation of Example 11 described in procedure G of Example 11. LC/MS; (M+H)$^+$=543.

Example 13

N-(1-(4-fluorophenylsulfonyl)azetidin-3-yl)-3-(2-phenyl-1H-pyrrolo[2,3-b]pyridin-5-ylthio)benzamide

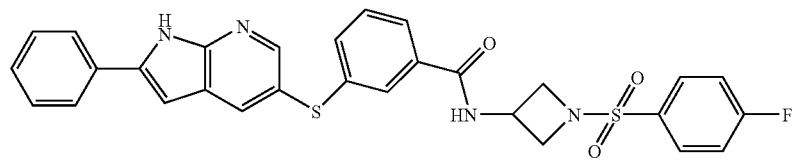

A) A procedure described in Syn. Lett. 1254, 2004 was followed. To solution of 2-amino-5-iodopyridine (220 mg, 1 mmol) in dimethyl formamide (2 mL) were added sequentially 3-mercaptobenzoic acid (185 mg, 1.2 mmol), CuI (50 mg), N,N-dimethylglycine (50 mg) and K$_3$PO$_4$ (1.06 g). The mixture was heated to 120° C. for 2 h, cooled to RT and water was added. The solid was filtered and the filtrate was treated with 1N HCl to adjust the solution to pH 4. The solid formed was collected by filtration, dissolved in 1N NaOH and the solution was filtered. The filtrate was purified by RP HPLC eluting with a mixture of methanol in water containing 0.1% TFA to obtain 3-(6-aminopyridin-3-ylthio)benzoic acid (84 mg, 34%). LC/MS; (M+H)+=247.

B) Compound A of this example was converted to the title compound by following the procedures described in the steps B to Steps G of the preparation of Example 11. LC/MS; (M+H)$^+$=559.

Example 14

N-(1-(4-fluorophenylsulfonyl)piperidin-4-yl)-3-(2-phenyl-1H-pyrrolo[2,3-b]pyridin-5-ylthio)benzamide

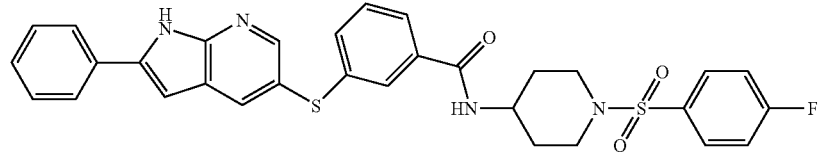

A) Compound A of Example 13 was converted to the title compound in a manner similar to the procedures described in the step B to step G of the preparation of Example 11. LC/MS; (M+H)$^+$=587.

Example 15

N-(3-(cyclopropylcarbamoyl)phenyl)-2-phenyl-1H-pyrrolo[2,3-b]pyridine-5-carboxamide

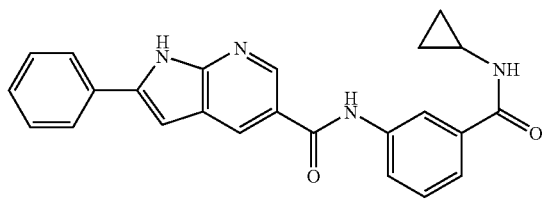

A) To a solution of 2-phenyl-1H-pyrrolo[2,3-b]pyridine-5-carboxylic acid (238 mg, 1 mmol, compound B of Example 1) in dimethyl formamide (5 mL) were added sequentially, methyl-3-aminobenzoate (151 mg, 1 mmol), triethylamine (0.1 mL) and BOP (500 mg, 1.2 mmol). After stirring the mixture at RT for 16 h, water was added and the solid formed was filtered, washed sequentially with water, 1N HCl, NaHCO$_3$ and water to afford methyl 3-(2-phenyl-1H-pyrrolo[2,3-b]pyridine-5-carboxamido)benzoate (100 mg) as a beige solid. LC/MS; (M+H)$^+$=372.

B) To a solution of the compound A of this example (100 mg) in methanol (4 mL) was added aqueous LiOH (1 mL, 2M) and the mixture was heated to reflux. After 4 h, the mixture was concentrated to remove methanol and 1N HCl (2 mL) was added to precipitate out the product. The solid was filtered, washed with water and dried in vacuo to afford 3-(2-phenyl-1H-pyrrolo[2,3-b]pyridine-5-carboxamido)benzoic acid (64 mg, 80% pure by HPLC). The crude product was used in the next step without further purification. LC/MS; (M+H)$^+$=358.

C) To a solution of compound B of this example (18 mg, 80% pure) in dimethyl formamide (1 mL) at RT were added BOP (40 mg) and cyclopropylamine (0.05 mL). After stirring for 30 min, the reaction mixture was purified by RP HPLC eluting with a mixture of methanol in water containing 0.1% TFA. The fractions containing the product were collected, concentrated, and neutralized with NaHCO$_3$ solution. The solid obtained was filtered, washed with water, and dried in vacuo to afford the title compound (11 mg). LC/MS; (M+H)$^+$=397.

We claim:
1. A compound of formula (I):

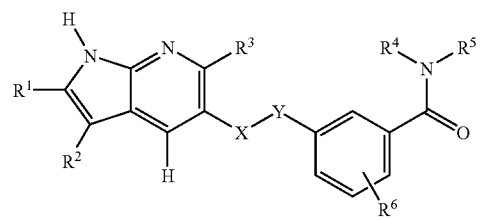

wherein
X and Y are independently —CH$_2$—, —NH—, —S— or —O—, or one of X and Y is absent;
R$^1$, R$^2$ and R$^3$ are independently hydrogen, alkyl, substituted alkyl, cycloalkyl, substituted cycloalkyl, aryl, substituted aryl, heteroaryl, substituted heteroaryl, heterocycloalkyl, substituted heterocycloalkyl, aryloxy or substituted aryloxy;
R$^4$ and R$^5$ are independently hydrogen, alkyl, substituted alkyl, aryl, substituted aryl, cycloalkyl, substituted cycloalkyl, heterocyclyl or substituted heterocyclyl, or
R$^4$ and R$^5$ are taken together with the nitrogen atom to which they are attached to form an optionally substituted heterocyclyl ring;
R$^6$ is independently one or more hydrogen, alkyl, substituted alkyl, aryl, substituted aryl, cyano or halogen,
or a pharmaceutically acceptable salt or stereoisomer thereof.

2. The compound according to claim 1 wherein:
X is —CH$_2$—, Y is —NH— or one of X and Y is absent and the other is —O— or —S—;
R$^1$, R$^2$ and R$^3$ are independently hydrogen, aryl, substituted aryl, heteroaryl, substituted heteroaryl, cycloalkyl or substituted cycloalkyl; and
R$^4$ and R$^5$ are independently hydrogen, cycloalkyl, substituted cycloalkyl heterocyclyl and substituted heterocyclyl.
or a pharmaceutically acceptable salt or stereoisomer thereof.

3. A compound selected from the group consisting of:
N-cyclopropyl-4-fluoro-3-{(2-phenyl-1H-pyrrolo[2,3-b]pyridin-5yl)methylamino}benzamide,
N-cyclopropyl-2,4-difluoro-5-((2-phenyl-1H-pyrrolo[2,3-b]pyridin-5-yl)methylamino)benzamide
N-cyclopropyl-4-fluoro-3-((2-phenyl-1H-pyrrolo[2,3-b]pyridin-5-ylamino)methyl)benzamide
N-cyclopropyl-3-((2-cyclopropyl-1H-pyrrolo[2,3-b]pyridin-5-yl)methylamino)-4-fluorobenzamide N-cyclopropyl-4-fluoro-3-((2-(pyridin-3-yl)-1H-pyrrolo[2,3-b]pyridin-5-yl)methylamino)benzamide N-cyclopropyl-4-fluoro-3-((2-(pyridin-2-yl)-1H-pyrrolo[2,3-b]pyridin-5-yl)methylamino)benzamide N-cyclopropyl-4-fluoro-3-((2-(4-methoxyphenyl)-1H-pyrrolo[2,3-b]pyridin-5-yl)methylamino)benzamide N-cyclopropyl-3-((2-(3-(2-(dimethylamino)ethoxy)phenyl)-1H-pyrrolo[2,3-b]pyridin-5-yl)methylamino)-4-fluorobenzamide N-(1-(4-fluorophenylsulfonyl)piperidin-4-yl)-3-(2-phenyl-1H-pyrrolo[2,3-b]pyridin-5-yloxy)benzamide N-(1-(4-fluorophenylsulfonyl)azetidin-3-yl)-3-(2-phenyl-1H-pyrrolo[2,3-b]pyridin-5-yloxy)benzamide N-(1-(4-fluorophenylsulfonyl)azetidin-3-yl)-3-(2-phenyl-1H-pyrrolo[2,3-b]pyridin-5-ylthio)benzamide N-(1-(4-fluorophenylsulfonyl)piperidin-4-yl)-3-(2-phenyl-1H-pyrrolo[2,3-b]pyridin-5-ylthio)benzamide N-(3-(cyclopropylcarbamoyl)phenyl)-2-phenyl-1H-pyrrolo[2,3-b]pyridine-5-carboxamide 2-phenyl-1H-pyrrolo[2,3-b]pyridine-5-carbonitrile 3-((4-aminopiperidin-1-yl)methyl)-2-phenyl-1H-pyrrolo[2,3-b]pyridine-5-carbonitrile;

or a pharmaceutically acceptable salt or stereoisomer thereof.

4. A pharmaceutical composition comprising one or more of the compounds of claim 1 and a pharmaceutically acceptable carrier.

5. A pharmaceutical composition comprising one or more of the compounds of claim 1 in combination with a pharmaceutically acceptable carrier and one or more other anti-cancer or cytotoxic agent.

* * * * *